US010880086B2

(12) United States Patent
Reed et al.

(10) Patent No.: US 10,880,086 B2
(45) Date of Patent: Dec. 29, 2020

(54) SYSTEMS AND METHODS FOR AUTHENTICATING A USER ON AN AUGMENTED, MIXED AND/OR VIRTUAL REALITY PLATFORM TO DEPLOY EXPERIENCES

(71) Applicant: PracticalVR Inc., Carrollton, TX (US)

(72) Inventors: James-Micheal A. Reed, Shreveport, LA (US); Terry L. Bennett, Sherman, TX (US); Volkan Seymen, Istanbul (TR)

(73) Assignee: PracticalVR Inc., Sherman, TX (US)

( * ) Notice: Subject to any disclaimer, the term of this patent is extended or adjusted under 35 U.S.C. 154(b) by 701 days.

(21) Appl. No.: 15/584,787

(22) Filed: May 2, 2017

(65) Prior Publication Data
US 2018/0323972 A1 Nov. 8, 2018

(51) Int. Cl.
*H04L 9/30* (2006.01)
*G06F 21/36* (2013.01)
(Continued)

(52) U.S. Cl.
CPC ............ *H04L 9/3066* (2013.01); *G06F 1/163* (2013.01); *G06F 3/011* (2013.01); *G06F 3/012* (2013.01);
(Continued)

(58) Field of Classification Search
CPC ............ H04W 12/04; H04W 12/0401; H04W 12/0608; H04W 12/06; H04W 4/02; G06F 3/04842; G06F 1/163; G06F 3/013; G06F 3/011; G06F 3/012; G06F 21/36; G06F 21/44; G06F 21/31; G06F 2221/2129; H04L 67/38; H04L 9/0822; H04L 9/0863; H04L 9/3066; H04L 9/3247; G06Q 20/3674; G06Q 20/4014; G06Q 30/02; G06Q 50/01; G02B 27/017;
(Continued)

(56) References Cited

U.S. PATENT DOCUMENTS 7,029,121 B2 4/2006 Edwards
7,409,543 B1 8/2008 Bjorn
(Continued)

FOREIGN PATENT DOCUMENTS

JP 2012047945 A 3/2012

OTHER PUBLICATIONS

PCT Search Report and Written Opinion, dated Oct. 4, 2018.
(Continued)

*Primary Examiner* — Kambiz Zand
*Assistant Examiner* — Benjamin A Kaplan
(74) *Attorney, Agent, or Firm* — Kirby Drake

(57) ABSTRACT

Systems and methods for authenticating a user on an augmented, mixed and/or virtual reality platform are provided. Once the user is authenticated, advertisements, experiences, appless apps, and/or tools may be deployed to a user, such as transforming an object on gaze into an advertisement, experience, scripted or un-scripted 3D object, animated or still 2D image, appless app, and/or tool. Using augmented, mixed and/or virtual reality technology, when a user looks/gazes at a virtual object, the bubble may then pop, transitioning into a video screen. The video screen is not being augmented on the virtual object itself.

7 Claims, 8 Drawing Sheets

(51) Int. Cl.

| | | |
|---|---|---|
| *G06F 3/01* | (2006.01) | |
| *G06Q 20/36* | (2012.01) | |
| *G06F 21/31* | (2013.01) | |
| *G06F 21/44* | (2013.01) | |
| *H04L 9/32* | (2006.01) | |
| *G06F 1/16* | (2006.01) | |
| *H04L 9/08* | (2006.01) | |
| *H04L 29/06* | (2006.01) | |
| *G06F 3/0484* | (2013.01) | |
| *G06Q 20/40* | (2012.01) | |
| *H04W 12/04* | (2009.01) | |
| *H04W 12/06* | (2009.01) | |
| *G06T 19/00* | (2011.01) | |
| *G02B 27/01* | (2006.01) | |
| *G06Q 30/02* | (2012.01) | |
| *G06Q 50/00* | (2012.01) | |
| *A61B 3/113* | (2006.01) | |
| *H04W 4/02* | (2018.01) | |

(52) U.S. Cl.
CPC ............ *G06F 3/013* (2013.01); *G06F 3/017* (2013.01); *G06F 3/04842* (2013.01); *G06F 21/31* (2013.01); *G06F 21/36* (2013.01); *G06F 21/44* (2013.01); *G06Q 20/3674* (2013.01); *G06Q 20/4014* (2013.01); *H04L 9/0822* (2013.01); *H04L 9/0863* (2013.01); *H04L 9/3247* (2013.01); *H04L 67/38* (2013.01); *H04W 12/0401* (2019.01); *H04W 12/0608* (2019.01); *A61B 3/113* (2013.01); *G02B 27/0172* (2013.01); *G06F 2221/2129* (2013.01); *G06Q 30/02* (2013.01); *G06Q 50/01* (2013.01); *G06T 19/006* (2013.01); *H04W 4/02* (2013.01)

(58) Field of Classification Search
CPC ........ G02B 2027/0187; G02B 27/0172; G02B 2027/014; G06T 19/006; A61B 3/113
USPC ....................................................... 380/283
See application file for complete search history.

(56) References Cited

U.S. PATENT DOCUMENTS

| | | | |
|---|---|---|---|
| 7,503,653 B2 | 3/2009 | Endrikhovski et al. | |
| 8,154,615 B2 | 4/2012 | Fedorovskaya et al. | |
| 8,510,166 B2 | 8/2013 | Neven | |
| 8,996,510 B2 | 3/2015 | Karmarkar et al. | |
| 9,014,509 B2 | 4/2015 | Fedorovskaya et al. | |
| 2005/0047629 A1 | 3/2005 | Farrell et al. | |
| 2006/0256133 A1 | 11/2006 | Rosenberg | |
| 2007/0100762 A1 | 5/2007 | Luo et al. | |
| 2007/0228179 A1 | 10/2007 | Atkinson | |
| 2008/0165955 A1 | 7/2008 | Ibrahim | |
| 2008/0252850 A1 | 10/2008 | Plagwitz et al. | |
| 2009/0097657 A1 | 4/2009 | Scheidt et al. | |
| 2010/0245352 A1 | 9/2010 | Chakraborty | |
| 2011/0150283 A1 | 6/2011 | Kim et al. | |
| 2012/0158502 A1 | 6/2012 | Chung et al. | |
| 2012/0226983 A1 | 9/2012 | Goldenberg et al. | |
| 2012/0257035 A1 | 10/2012 | Larsen | |
| 2012/0284517 A1 | 11/2012 | Lambert | |
| 2013/0138499 A1 | 5/2013 | Tu et al. | |
| 2013/0254536 A1 | 9/2013 | Glover | |
| 2014/0025582 A1 | 1/2014 | Maevsky | |
| 2014/0089097 A1 | 3/2014 | Byun et al. | |
| 2014/0125574 A1 | 5/2014 | Scavezze et al. | |
| 2014/0294175 A1 | 10/2014 | Boloker et al. | |
| 2014/0379485 A1 | 12/2014 | Goswami et al. | |
| 2015/0006278 A1 | 1/2015 | Di Censo et al. | |
| 2015/0042953 A1 | 2/2015 | Teller | |
| 2015/0058102 A1 | 2/2015 | Christensen et al. | |
| 2015/0199729 A1 | 7/2015 | Saccoman | |
| 2015/0304369 A1 | 10/2015 | Sandholm et al. | |
| 2016/0012475 A1 | 1/2016 | Liu | |
| 2016/0027218 A1 | 1/2016 | Salter et al. | |
| 2016/0179336 A1* | 6/2016 | Ambrus | G02B 27/017 715/768 |
| 2016/0216761 A1 | 7/2016 | Klingstrom et al. | |
| 2016/0283941 A1 | 9/2016 | Andrade | |
| 2016/0379409 A1 | 12/2016 | Gavrilluc et al. | |
| 2017/0061396 A1 | 3/2017 | Melika et al. | |
| 2017/0085545 A1 | 3/2017 | Lohe et al. | |
| 2017/0178408 A1* | 6/2017 | Bavor, Jr. | G06F 3/013 |
| 2017/0280129 A1* | 9/2017 | Mirota | G06T 7/70 |
| 2017/0371403 A1* | 12/2017 | Wetzler | G06F 3/00 |

OTHER PUBLICATIONS

Notification of Transmittal of the International Search Report and the Written Opinion of the International Searching Authority or the Declaration, PCT/US18/30291, dated Oct. 4, 2018, 20 pages, International Searching Authority.

* cited by examiner practicalVR:
Ad transition to Video

Spawn

301a

Gaze

302a

Transition

303a

Display AD Video

304a practicalVR:
Ad transition to aCommerce

Spawn

301b

Gaze

302b

Transition

303b

Display aCommerce

304b practicalVR:
Ad transition to Experience

Spawn

301c

Gaze

302c

Transition

303c

304c

| Practical<sup>VR</sup> : Event Manager | | |
|---|---|---|
| One or more servers connects to the Practical manager and authenticates the client using the Practical key.<br />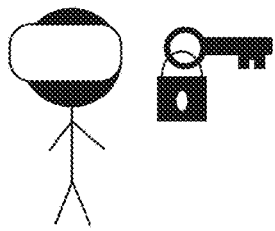　501 | Once authenticated, server sends data to the Practical manager on the client<br />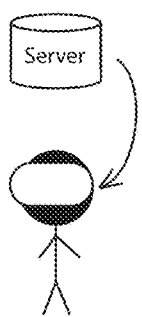　502 | Through such events, the Practical Event Manager may spawn additional child managers. Including but not limited to an ad event manager.<br />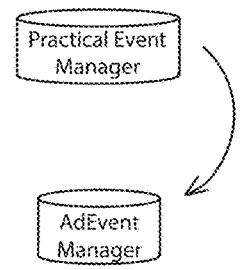　503 |
| The Ad Event Manager contains various elements such as models, metadata, video stream, etc.<br />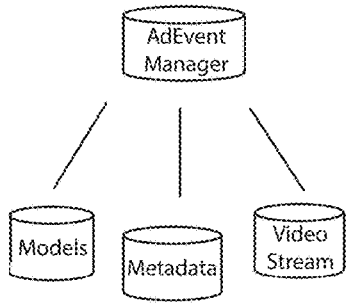　504 | The Practical Event Manager also may handle the dynamic and room contextual spawning of the ad object in embodiments of the present disclosure.<br />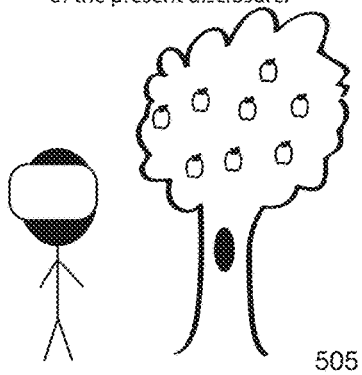　505 | In some embodiments of the present disclosure, a collection event manager also may be present or logic may be included within another manager to collect data for storage or help improve ad targeting.<br />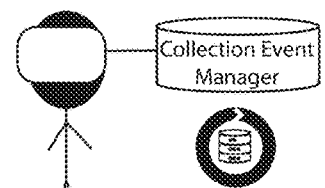　506 |

*FIG. 5*

| Practical<sup>VR</sup> : Collection Manager | | |
|---|---|---|
| One or more servers connects to the Practical manager and authenticates the client using the Practical key.<br />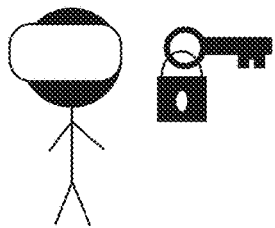　601 | Once authenticated, server sends data to the Practical manager on the client<br />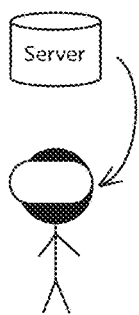　602 | Through such events, the Practical Event Manager may spawn additional child managers. Including but not limited to an Collection manager.<br />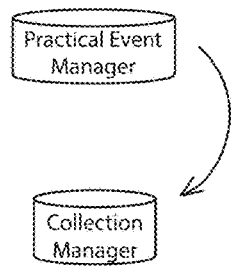　603 |
| The Collection Manager contains logic for data collection.<br />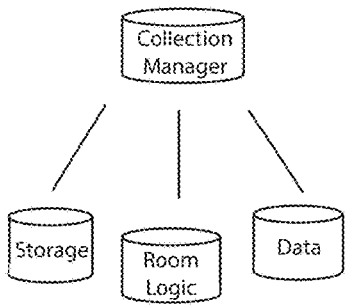　604 | The Practical Event Manager also may handle the dynamic and room contextual spawning of the ad object in embodiments of the present disclosure.<br />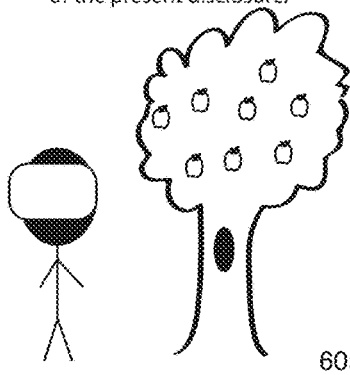　605 | In some embodiments of the present disclosure, a collection event manager also may be present or logic may be included within another manager to collect data for storage or help improve ad targeting.<br />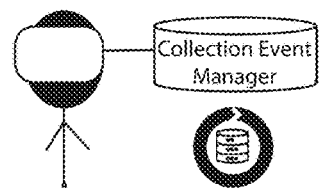　606 |

*FIG. 6*

SYSTEMS AND METHODS FOR AUTHENTICATING A USER ON AN AUGMENTED, MIXED AND/OR VIRTUAL REALITY PLATFORM TO DEPLOY EXPERIENCES

FIELD OF THE DISCLOSURE

The present disclosure generally relates to authentication of a user on an augmented, mixed and/or virtual reality platform, and more particularly to authentication to deploy advertisements, experiences, scripted and non-scripted 3D objects, animated or still 2D images, appless apps, and/or tools to a user.

BACKGROUND

Headsets have been developed focused on virtual reality, but there are challenges with respect to screen resolution as well as the refresh rate of the screen. When moving into augmented reality, there are even more challenges with respect to the headset and its capabilities because augmented reality requires understanding the environment around the user of a headset. While some headsets have been developed to focus on augmented reality, challenges have been faced in providing the processing power to process large amounts of spatial data while rendering holograms in real-time for display to a user. Further, augmented reality headsets have been limited in their applications.

SUMMARY

Embodiments of the present disclosure may provide a method for authenticating a user on an augmented, mixed or virtual reality platform, the method comprising: upon connection between a client and at least one server after the user launches an application on the augmented, mixed or virtual reality platform, checking to see if an existing practical key for the user is stored; using the existing practical key, reading a public key and an encrypted private key; sending the public key to the at least one server; receiving a saved password; decrypting the private key and signing a message to include a cryptographic signature; sending the cryptographic signature to the at least one server for verification; receiving a new password from the at least one server, wherein the new password may be used to re-encrypt the private key; notifying the at least one server that the practical key has been saved; and receiving confirmation that the user is authenticated, wherein upon authentication of the user, one or more experiences may be deployed to the user. The connecting step may be performed via a websocket or an HTTPS connection. The method also may comprise creating a cryptographic key pair if no existing practical key for the user is stored; sending a public key to seek new authentication; and receiving a password to be used to encrypt a private key. The one or experiences may comprise transformation, spawning, or location locking of at least one object and triggered by gaze into one or more of the following: an advertisement, experience, scripted and non-scripted 3D object, animated or still 2D image, appless app or tool. The transformation may further comprise sending raycasts in a direction that the user is gazing; placing the at least one object into an environment; and when one of the raycasts collides with the at least one object, triggering a transition that transforms the at least one object into the advertisement, experience, scripted or un-scripted 3D object, animated or still 2D image, appless app or tool. Location locking may further comprise utilization of spatial mapping data, geo-location, and/or other methods of anchoring objects to a precise location of a room, outside placement, and/or building exterior stored on one or more servers for real-time deployment of the one or more experiences. The advertisement, experience, scripted or un-scripted 3D object, animated or still 2D image, appless app, or tool may comprise one or more of the following: a video, a character, a billboard, aCommerce, a survey, a 3D model, a 2D interface, an animated or non-animated image, an experience, or other interface for input. The method also may comprise adjusting the advertisement, experience, scripted or un-scripted 3D object, animated or still 2D image, appless app, or tool based on one or more factors selected from the following: an optimal height of a display of the advertisement, experience, scripted or un-scripted 3D object, animated or still 2D image, appless app, or tool, speed at which the advertisement, experience, scripted or un-scripted 3D object, animated or still 2D image, appless app, or tool is displayed based on engagement traced by the user's gaze, presence of more than one user, duration of time since the user has viewed the advertisement, experience, scripted or un-scripted 3D object, animated or still 2D image, appless app, or tool, and speed and direction of movement associated with the advertisement, experience, scripted or un-scripted 3D object, animated or still 2D image, appless app, or tool. The one or more experiences may comprise spawning of at least one object triggered by keyword, hand gesture, computer vision recognized object, eye-movements, or other user controlled action, into one or more of the following: an advertisement, experience, scripted or un-scripted 3D object, animated or still 2D image, appless app or tool. The one or more experiences may comprise spawning of at least one object triggered by gesture into one or more of the following: an advertisement, experience, scripted or un-scripted 3D object, animated or still 2D image, appless app or tool. The existing practical key for the user may be stored via cryptographic keyring, folder, or embedded within an image (PNG, JPG, GIF) or other file on an augmented, mixed, or virtual reality device. The data associated with the practical key may be embedded within or appended to data associated with an image. Elliptical curve key data may be embedded within an image and read to facilitate authentication on the augmented, mixed or virtual reality platform. An elliptical curve key may be used in combination with the augmented, mixed or virtual reality platform to create, use, or facilitate a cryptocurrency wallet. An elliptical curve key may be used for authentication and identification on the augmented, mixed or virtual reality platform to enable dynamic or static deployment of content selected from the group comprising: an advertisement, an experience, scripted or un-scripted 3D object, animated or still 2D image, appless app or tool. An elliptical curve key may be embedded on an augmented, mixed or virtual reality device and may be used to encrypt collected data. An elliptical curve key embedded on an augmented, mixed or virtual reality device may be used in combination with other data to act as a profile that enables user-to-user communication. An elliptical curve key embedded on an augmented, mixed or virtual reality device may be used to encrypt user-to-user communications deployed as a holographic object or 2D interface within another experience. An elliptical curve key embedded on an augmented, mixed or virtual reality device may be used as a cryptocurrency wallet to sign a message creating a transaction that may be represented visually as a holographic object, 3D object, particle effect, or 2D notification with or without sound. An elliptical curve public key embedded on an augmented, mixed or virtual reality device may be capable of being shared as an image or 3D object, added to a friend list, and used for permissioned sharing of content selected from the group comprising: an advertisement, experience, scripted or un-scripted 3D object, animated or still 2D image, appless app or tool. The one or more experiences, may comprise one or more of the following: transfer of cryptocurrency via a motion, gesture, or eye movement, toward a physical object, a holographic object, a 2D interface, a location, a company logo, website content, or another person, playing games, rewarding or providing feedback on an action or gesture based on confirmed recognition from input data gathered from the user via the augmented, mixed, or virtual reality platform, creation, transfer or deletion of data, database searching, and sharing of experiences and placement of content with other users. Upon authentication of the user, data may be collected from the user, the data including tags based on gestures and/or actions of the user, gaze patterns of the user, duration of gaze of the user, distance traveled to shop, types of stores visited, environment mapping, transactions made via the augmented, mixed or virtual reality platform, engagement level based on surveys, placed or spawned location of experiences, scripted or un-scripted 3D objects, animated or still 2D images, appless apps, and/or tools, and/or ad campaign participation.

Other embodiments of the present disclosure may provide a method for spawning or transformation of an object or an interface on action by a user on an augmented, mixed or virtual reality platform upon authentication of the user, the method comprising: starting a practical event manager, wherein a session is created and the user is identified; loading location-locked objects and/or placing an object dynamically into an environment being viewed by the user in a main experience, wherein the object passively waits for a collision with a raycast from the user or interaction via action by the user; and starting a transition once the object detects the raycast from collision or action, wherein the transition transforms the object into one or more additional experiences. The method may further comprise placing a duplicate object into the environment after a period of time has passed and no collision with the raycast or action has occurred. When the transition or interaction starts, the main experience may enter a frozen state to prevent interruption of the main experience. The one or more additional experiences may be selected from the group comprising: a video, a character, a billboard, aCommerce, a survey, a 3D model, a 2D interface, an animated or non-animated image, an experience, or other interface for input. Upon authentication of the user, data may be collected from the user, the data including tags based on gestures and/or actions of the user, gaze patterns of the user, duration of gaze of the user, distance traveled to shop, types of stores visited, transactions made via the augmented, mixed or virtual reality platform, engagement level based on surveys, placed or spawned location of experiences, scripted or un-scripted 3D objects, animated or still 2D images, appless apps, and/or tools, and/or ad campaign participation. The user may be identified through the following steps: upon connection between a client and at least one server after the user launches an application on the augmented, mixed, or virtual reality platform, checking to see if an existing practical key for the user is stored; using the existing practical key, reading a public key and an encrypted private key; sending the public key to the at least one server; receiving a saved password; decrypting the private key and signing a message to include a cryptographic signature; sending the cryptographic signature to the at least one server for verification; receiving a new password from the at least one server, wherein the new password is used to re-encrypt the private key; notifying the at least one server that an encrypted practical key has been saved; and receiving confirmation that the user is authenticated. The action may be selected from the group comprising: gaze, keyword, hand gesture, computer vision recognized object, eye movements, or other user-controlled action.

Further embodiments may provide a practical key comprising: a block of information including a public key and an encrypted private key combined with one or more pieces of data and stored within a folder, image, 3D object or file on an augmented, mixed or virtual reality platform, wherein the block of information may further include an indicator for use as a profile for identification and authentication on the augmented, mixed or virtual reality platform. The public key and the encrypted private key may be compressed or uncompressed. The practical key may be transferred or duplicated to one or more devices and used for authentication and identification purposes. The encrypted private key may be encrypted by a password stored within one or more servers. The encrypted private key may be encrypted by a local method of encryption. The public key may be sharable for quick identification, communication and sharing of content on the augmented, mixed or virtual reality platform through one or more methods selected from the group comprising: an image, text, animation, and a list. The content may be selected from the group comprising: advertisements, experiences, scripted and non-scripted 3D objects, animated and still 2D images, appless apps, and tools. The practical key may be integrated within a third-party authentication system to authenticate users within applications, websites or other mediums that require identification and verification of the users. The practical key may include a permission system to customize what the practical key shares publicly. The permission system may include one or more levels of permissions customizable on an individual or entity level. The public key may be continuously broadcast based on location to other devices over a wireless and/or physical conduction technology. Sharing permissions may be continuously broadcast to other devices and/or one or more servers over a wireless and/or physical conduction technology. The practical key may enable a user to review statistics that are visually represented using one or more of the following: a 2D interface, 3D object, appless app, application, website interface, tool, synthesized voice, gesture, keyword, gaze, eye movement, and other forms of input. The practical key may perform the following steps: associate actions to a user's identity; add goals, milestones or other counters; and allow rewards for achievement. The practical key may be compatible with cryptocurrency.

BRIEF DESCRIPTION OF THE DRAWINGS

For a more complete understanding of this disclosure, reference is now made to the following description, taken in conjunction with the accompanying drawings, in which:

FIG. 5 depicts an event manager process according to an embodiment of the present disclosure; and FIG. 6 depicts a collection manager process according to an embodiment of the present disclosure.

DETAILED DESCRIPTION

Embodiments of the present disclosure may provide systems and methods for authenticating a user on an augmented, mixed and/or virtual reality platform. Once the user is authenticated, systems and methods according to embodiments of the present disclosure may deploy experiences to a user, such as enabling and/or transforming an object on gaze or other interaction into an advertisement or other experience, scripted or un-scripted 3D object, animated or still 2D image, appless app, and/or tool. As used herein, an "appless app" may be considered a smaller app within a larger, more-themed application. Tools can be of similar nature but standard (i.e., a calculator).

Using augmented and/or virtual reality technology, when a user looks/gazes at a virtual object, such as a bubble, the bubble may then pop, transitioning into an ad video screen. The ad video screen is not being augmented on the virtual object itself. As will be described further below, systems and methods according to embodiments of the present disclosure may be integrated with any application. In some embodiments of the present disclosure, data also may be collected.

Figure 1:
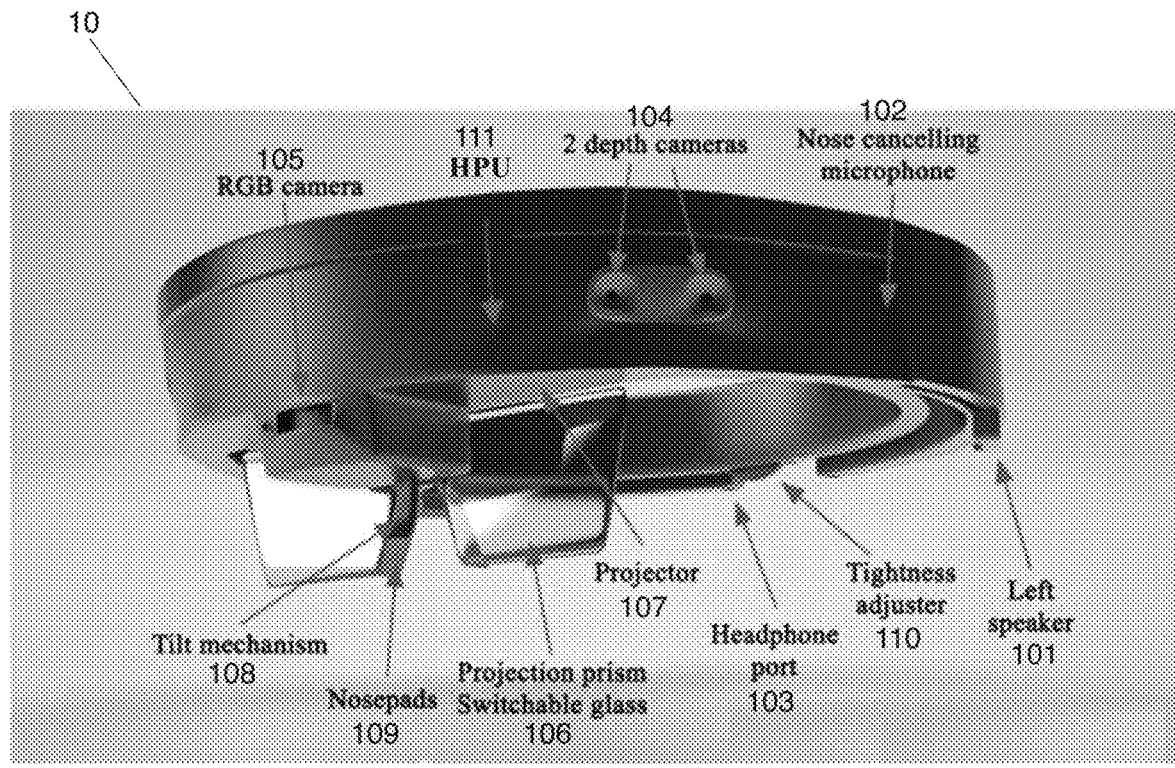
FIG. 1 depicts an AV/VR headset according to an embodiment of the present disclosure.

FIG. 1 depicts AV/VR headset 10 according to an embodiment of the present disclosure. It should be appreciated that headset 10 may be untethered and self-contained so that no PC or phone is required to use headset 10 and project holograms around the environment of a user wearing headset 10; however, there may be other embodiments wherein headset 10 may be tethered or in communication with a PC or phone without departing from the present disclosure. If headset 10 is untethered, it may include a battery in order to power headset 10. Headset 10 may be a display device paired to a user's forehead area with a headband extending around the crown of the user's head. Headset 10 may include speaker 101 that may provide a user with an audio experience internal to headset 10, and headset 10 also may include at least one microphone 102 so that the user may provide commands and/or respond as well as headphone port 103. At least one microphone 102 may be noise-cancelling so that the user of headset 10 may be less distracted by noise external to the AV/VR experience.

At least one depth camera 104 as well as at least one RGB camera 105 in conjunction with projection prism switchable glass 106, projector 107 and tilt mechanism 108 may enable the AV/VR experience for the user of headset 10. At least one depth camera 104 may assist with hand tracking as well as surface reconstruction, which may enable placement of holograms on physical objects as will be described in more detail below. In an embodiment of the present disclosure, there may be two depth cameras 104; however, there may be more than two depth cameras 104 without departing from the present disclosure. At least one RGB camera 105 may survey a room so that headset 10 may know where items are positioned within the room, and use that information to project three-dimensional images around the room. RGB camera 105 may sit above the visor portion at the front of headset 10 and work in tandem with the at least one depth camera 104, which may be positioned on either side of headset 10. Working together, these cameras may capture the environment around the user and help headset 10 to understand where the boundaries in a room are. While several cameras may be included in headset 10, it should be appreciated that more or fewer cameras may be incorporated into headset 10 without departing from the present disclosure. Projector 107 may be a liquid crystal on silicon (LQoD) display, and there may be more than one projector 107 in embodiments of the present disclosure. Projector 107 may be mounted on the bridge of the lenses of headset 10 to shoot out images. Nosepads 109 and tightness adjuster 110 may be included as part of headset 10 to make use of headset 10 more comfortable for the user. It should be appreciated that other display technologies may be utilized without departing from the present disclosure. These display technologies may include, but are not limited to, projection of light fields directly into a user's eyes to produce an image as well as use of a brain computer interface (BCI).

Headset 10 may include one or more processors (HPU) (111) that may operate using low amounts of power (typically under 10W of power). It should be appreciated that headset 10 should have enough processing power as may be needed to understand the user's gestures, gaze, voice, as well as the environment around the user. In embodiments of the present disclosure, in addition to the one or more processors, headset 10 may include RAM, flash memory, a Wi-Fi chip, a Bluetooth chip, a cellular chip, and other wireless communication technologies. The one or more processors also may be used to launch applications and display holograms to the user.

Headset 10 may track the wearer's movements, watch his/her gaze and transform what the wearer sees by directing light toward the wearer's eyes. Headset 10 may use one or more inputs, including but not limited to, gaze, gesture and voice to engage with the AR/MR/VR experience. Gaze inputs, such as head-tracking, may allow the user to bring focus to whatever the user is perceiving. Gesture inputs, such as an air tap or one-fingered, downward swipe, may allow the user to select a virtual application and/or interact with the three-dimensional images being displayed. Accordingly, a user of headset 10 may select an object, use his/her gaze to move the object around the room, and then use a gesture to lock the object in a new spot. As will be described in more detail below, headset 10 also may include spatial mapping and/or spatial audio without departing from the present disclosure.

In embodiments of the present disclosure, one or more applications that integrate systems and methods according to embodiments of the present disclosure (also referred to as the PracticalVR platform) may be published in one or more locations, such as the Windows AppStore. A user may select an application published in the one or more locations for download and then launch the selected application. After launching an application, a user may be authenticated through a process as depicted in FIG. 4.

Figure 4:
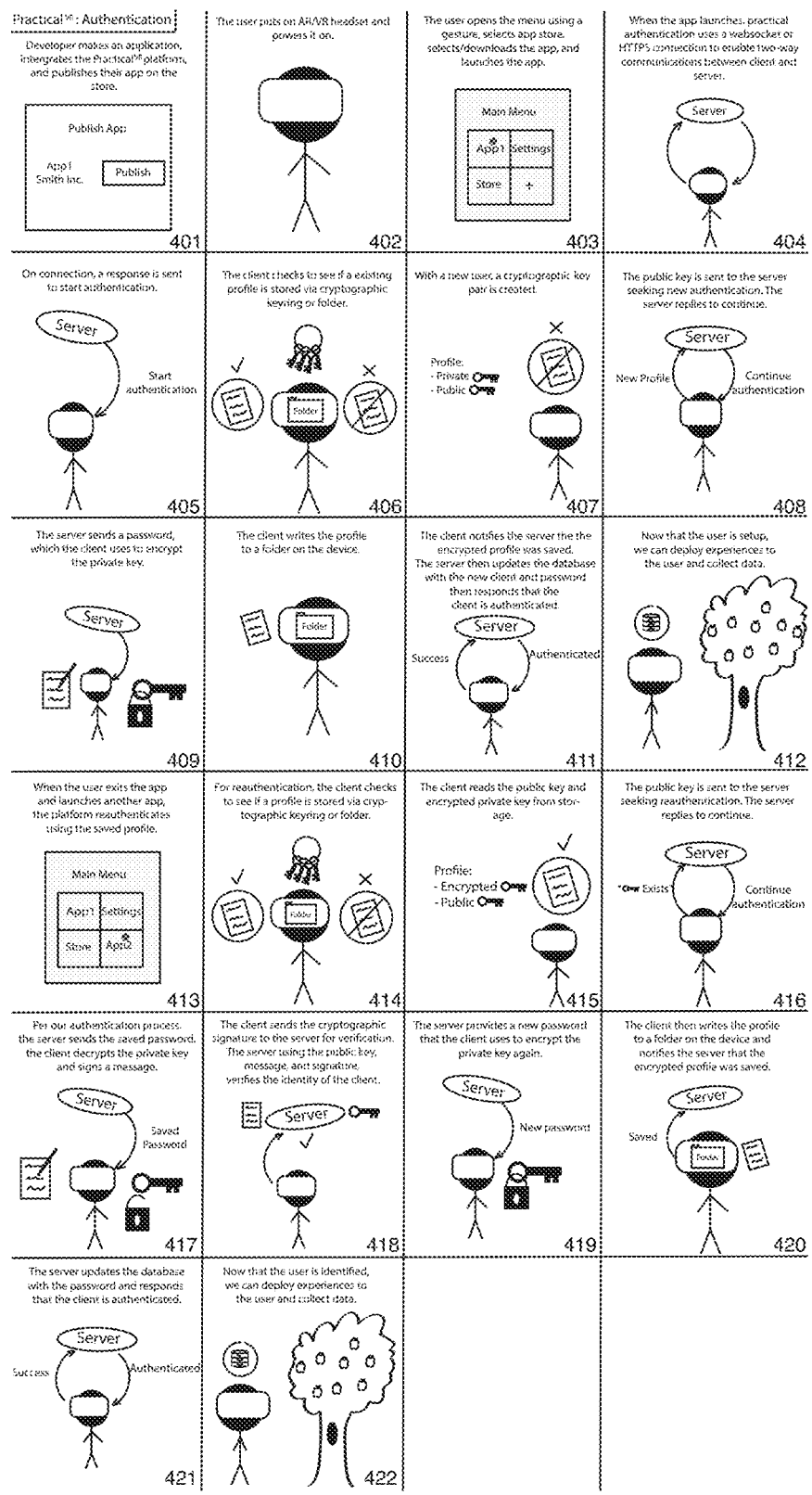
FIG. 4 depicts a process for authentication integrating the PracticalVR platform according to an embodiment of the present disclosure.

FIG. 4 depicts an authentication process according to an embodiment of the present disclosure. A developer may create an application, integrate the PracticalVR platform into the application, and publish the application in one or more locations, such as on the Windows AppStore (step 401). When a user is ready to utilize an application using the PracticalVR platform, a user may put on an AR/VR headset (such as headset 10 in FIG. 1) and power it on (step 402). The user may open a menu using a gesture within a location, such as the Windows AppStore, using a gesture and select/download an application that has integrated the PracticalVR platform and then launch the application (step 403). When referring to a "gesture," this may be an input that allows the user to interact with a hologram. A gesture input may allow a user to interact with the hologram naturally using his/her hands or, in some embodiments, using a clicker device, controller, glove, and/or other external sensory device. The headset may track the position of either or both of the user's hands that are visible to the headset. Gestures may include, but are not limited to, an air-tap, held air-tap, or a bloom. An air-tap may require a user to make a fist in front of his/her body with the back of the user's hand facing him/her. An air-tap may also be held in order to access additional options, or to manipulate an object such as rotation or scrolling. The user may then raise his/her index finger to the sky and then tap by flexing his/her finger down and then back up. An air-tap is similar to a mouse click. The bloom gesture may be used to allow a user to go back to the main menu from within an application. A user may hold out his/her hand, palm up, with fingertips together; then, the user may open his/her hand. While certain gestures have been described, it should be appreciated that other gestures, either alone or in combination with one another, may be utilized to dismiss and interact with ad objects without departing from the present disclosure.

When the application launches, an authentication process according to an embodiment of the present disclosure may use a websocket or HTTPS connection to enable two-way communications between the client and one or more servers (step 404). On connection, a response may be sent to start authentication (step 405). The client may check to see if an existing profile is stored via cryptographic keyring, folder, or embedded file (step 406). If the user is identified as a new user, a cryptographic key pair may be created (step 407). The profile may include a private key and a public key. It should be appreciated that the public key may serve as a user identification in systems and methods according to embodiments of the present disclosure, thereby avoiding collection of personal information such as an email address or username from the user for the purpose of account creation. The public key may be sent to the server seeking new authentication, and the one or more servers may reply to continue the authentication process (step 408). The one or more servers being utilized in the authentication process may then transmit a password, which the client may use to encrypt the private key (step 409). The client may then write the profile to a folder on the device being used (step 410). The client then may notify the one or more servers that the encrypted profile has been saved. The one or more servers may then update one or more databases to identify the new client and password. The one or more servers may then respond to confirm that the client has been authenticated (step 411). Once the user has been authenticated within the system, one or more advertisements, experiences, appless apps, and/or tools may be deployed to the user and data may be collected as will be described in more detail later (step 412).

The user may not remain within the initially-selected or first application and may choose to launch another application. When the user exits a first application and launches another application, the platform may re-authenticate the user using his/her saved practical key (referred to in FIG. 4 as profile) (step 413). A practical key may be automatically generated and provide secure authentication and anonymized identification. It may be embedded on a user's device in embodiments of the present disclosure. For re-authentication, the client may check to see if a practical key has been stored via cryptographic keyring or folder (step 414). Using the stored practical key, the client may read the public key and the encrypted private key (step 415). The public key may be sent to the one or more servers seeking re-authentication; the one or more servers may reply to continue (step 416). The one or more servers may then send the saved password, and the client may decrypt the private key and sign a message (step 417). The client then may send the cryptographic signature to the one or more servers for verification. Using the public key, the message, and the cryptographic signature, the one or more servers may verify the identity of the client (step 418). It should be appreciated that the message is being signed with the private key once encryption has been removed to verify the identity of the user. The one or more servers may then provide a new password that the client may use to re-encrypt the private key (step 419). It should be appreciated that the private key may be encrypted on the client side, and the password to the private key may be encrypted on the server side in embodiments of the present disclosure. The client then may write the practical key to a cryptographic keyring, folder, image (PNG, JPG, GIF), or other file on the device being used and notify the one or more servers that the practical key has been saved (step 420). The one or more servers may then update the database with the password and respond to confirm that the client has been authenticated (step 421). Once the user has been identified again, systems and methods according to embodiments of the present disclosure may be used to deploy advertisements, experiences, appless apps, scripted or unscripted 3D objects, 2D animated or still images, microtransactions, and/or tools to the user and collect data (step 422). As referred to herein, a "microtransaction" may be understand as payment or earning using cryptocurrency. A user may be paid for data that he/she shares (and the PracticalVR platform collects), the user's engagements with advertising or branded experiences, and/or other events defined by the PracticalVR platform or other parties. A user could then utilize his/her wallet for payments throughout the PracticalVR platform including appless app purchases, tools, skipping advertisements/branded content, digital and physical commerce purchases, and/or any other transaction later defined utilizing the practical key to facilitate a transaction. It should be appreciated that the one or more servers may not have access to or never see the unencrypted private key.

Figure 2:
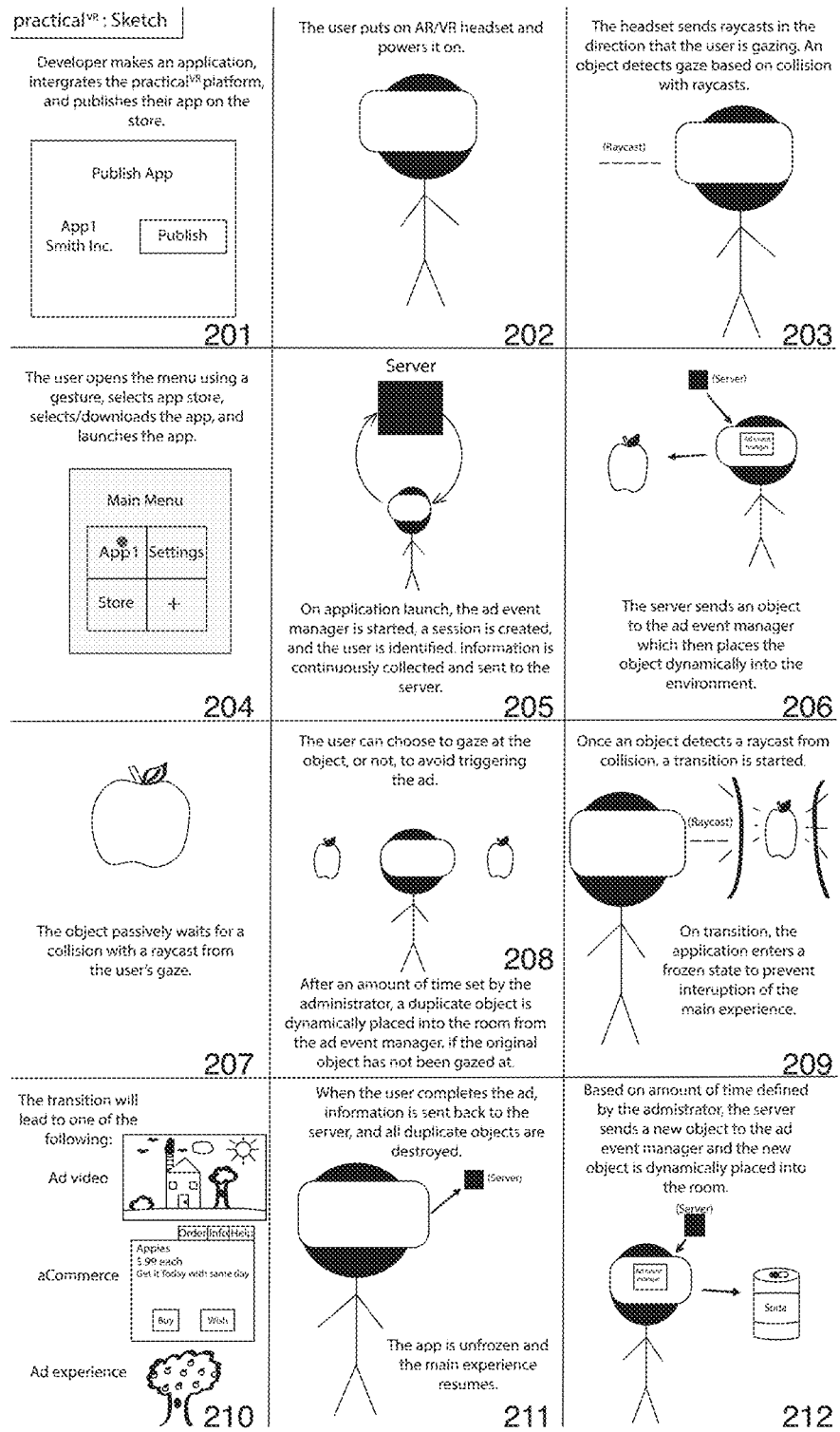
FIG. 2 depicts a process for using an application integrating the PracticalVR platform according to an embodiment of the present disclosure.

As previously discussed, once a user has been authenticated, advertisements, experiences, scripted or unscripted 3D objects, 2D animated or still images, appless apps, and/or tools may be deployed to the user. FIG. 2 depicts a process for using an application integrating the PracticalVR platform according to an embodiment of the present disclosure. Again, as previously discussed, a developer may create an application using their game engine or software of choice, integrate the PracticalVR platform and publish the application in one or more locations (step 201). In an embodiment of the present disclosure, the PracticalVR platform may allow a developer to drag and drop the platform into its scene and make calls to the API (such as Unity 3D API) that may handle communication to a dynamic-link library (DLL) or another shared library. The DLL may be ported to a platform, such as the Universal Windows Platform (UWP) to enable a secure method of authenticating users and communicating with the servers. This DLL may handle socket communications, key generation, message signing, and encryption, data collection, and may be compatible with any cryptocurrency. In embodiments of the present disclosure, Socket 10 may be used to facilitate bi-directional real-time communications with websockets. As the architecture of the PracticalVR platform is modular, subsystems may be scaled without the need for major rewrites of code to operate the platform.

When a user is ready to utilize an application using the PracticalVR platform, a user may put on an AR/VR headset (such as headset 10 in FIG. 1) and power it on (step 202).

Upon powering the headset on, the headset may send raycasts in the direction that the user is gazing (step 203). An object may detect gaze based on collision with raycasts. Raycasts may be used to determine the intersection of two objects, as would be known to one of ordinary skill in the art within the fields of computer graphics and computational geometry. In some embodiments of the present disclosure, the libraries available in the Unity Engine (https://docs.unity3d.com/ScriptReference/Physics.Raycast.html), may be used; however, there may be other embodiments of the present disclosure where additional or other libraries may be used, such as when different platforms and engines may be used.

The user may open a menu within a location, such as the Windows AppStore, using a gesture and select/download an application integrating the PracticalVR platform and then launch the application (step 204). On application launch, the practical event manager may be started, a session may be created, and the user may be identified (step 205). The practical event manager is the front-end handler that handles authentication (such as described in FIGS. 4 and 5) and receives events from the one or more servers. As depicted in FIG. 5, one or more servers may connect to the practical event manager and authenticate the client using the practical key (step 501). Once authenticated, the one or more servers may send data to the practical event manager on the client (step 502). Through such events, the practical event manager may spawn additional child managers, including but not limited to, an ad event manager (models, metadata, video stream, etc.) (steps 503, 504). It also may handle the dynamic and room contextual spawning of the ad object in embodiments of the present disclosure (step 505). In some embodiments of the present disclosure, a collection event manager also may be present to or logic may be included within another manager to collect data for storage or to help improve ad targeting, thereby acting as a door to the developer's application (step 506). The collection manager is depicted in more detail in FIG. 6. The steps in FIG. 6 are similar to those described with respect to the practical event manager except that in the embodiment of FIG. 6, an additional child manager may be a collection manager (step 603). The collection manager may contain logic for data collection (step 604). Data may be collected from one or more areas, including, but not limited to, gaze (as a user looks at hologram), gesture (as the user taps his/her finger), spatial (as the user maps a room around him/her), voice (any spoken keywords), and movement (as the user moves around a room). Developers may utilize a portal to see data collected from their apps in real-time. For example, the developer may be alerted to problems within his/her app (i.e., that objects are moving too fast for comfort), and the developer may fix the problem, update the app, and see results in real-time. While experiences have been described in the context of advertisement delivery/targeting, it should be appreciated that additional or other child managers may be utilized to deliver other experiences, appless apps, and/or tools or perform other tasks without departing from the present disclosure.

It should be appreciated that information may be continuously collected and sent to one or more servers. The one or more servers may send an object or additional child manager to the practical event manager and subsequently child managers which then may place the objects or other managers dynamically hidden or visible into the environment (step 206). There may be embodiments of the present disclosure where the logic from multiple managers are combined onto a single centralized manager or split into children to handle defined areas. As depicted in FIG. 2, the object is an apple or a hidden manager; however, other objects may be placed into the environment without departing from the present disclosure. The object may passively wait for an event from the server with further instructions, or if visible a collision with a raycast from the user's gaze (step 207). In some embodiments of the present disclosure, the user may choose to gaze at a visible object to trigger an event such as an advertisement, or choose not to gaze at the object in other embodiments of the present disclosure so as to avoid triggering the local event (step 208). After a predetermined period of time set by the administrator has elapsed, a duplicate visible object may be dynamically placed into the room using the responsible event manager, if the user has not yet gazed at the originally-placed object. As depicted in FIG. 2 (step 208), a duplicate apple has been placed into the environment.

Once an object detects a raycast from collision, a transition or other event may be triggered (step 209). On event, the application may enter a frozen state to prevent interruption of the main experience. A message may be passed from the server to the practical event manager and then depending on the type of event, passed to the corresponding event manager. In the example of an ad event, an event may cause a transition that leads to one or more of the following: an ad billboard, an ad video, aCommerce, a survey and an ad experience (step 210). Each of these actions will be described in more detail below. While certain actions have been identified, it should be appreciated that other actions may occur on transition without departing from the present disclosure.

When the user completes, for example, viewing an ad video, information may be sent back to the one or more servers, and all duplicate objects may be destroyed (step 211). The application may then be unfrozen and the main experience may resume. The main experience refers to the actual application itself. For example, a game may be considered the main experience. Pausing the main experience may keep the interruption and invasiveness to a minimum. Based on the predetermined amount of time defined by the administrator, the one or more servers may send a new object to the responsible event manager, and the new visible object may be dynamically placed into the environment (step 212). As depicted in FIG. 2, the new object may be a soda can.

Figure 3A:
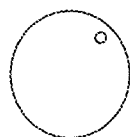
FIGS. 3A-3C depict various ad transitions according to embodiments of the present disclosure.
Figure 3A:
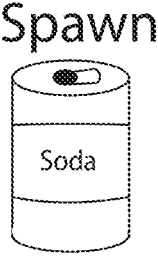
Figure 3A:
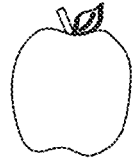
Figure 3A:
Figure 3A:
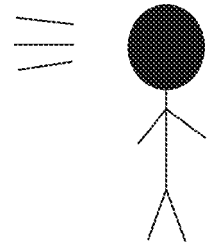
Figure 3A:
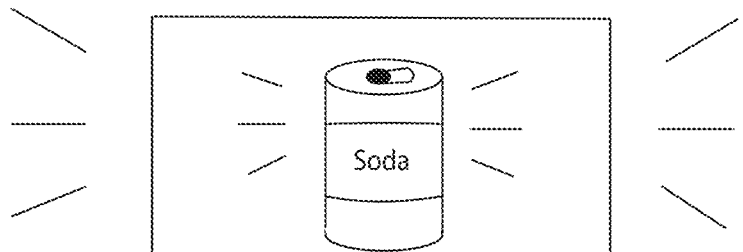
Figure 3A:
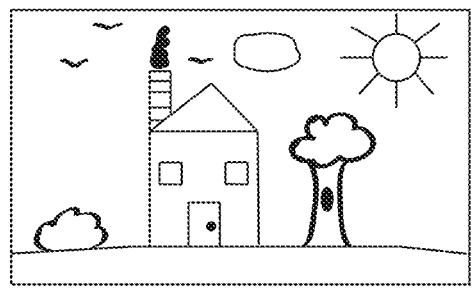
Figure 3B:
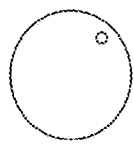
Figure 3B:
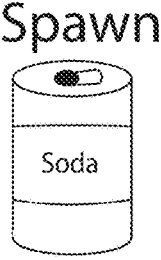
Figure 3B:
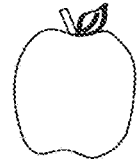
Figure 3B:
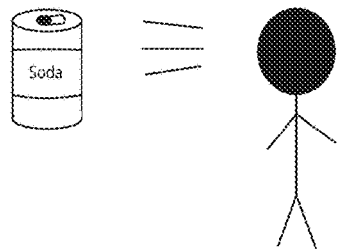
Figure 3B:
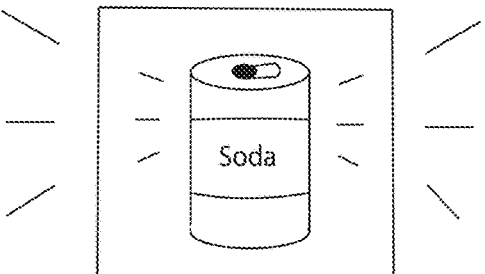
Figure 3B:
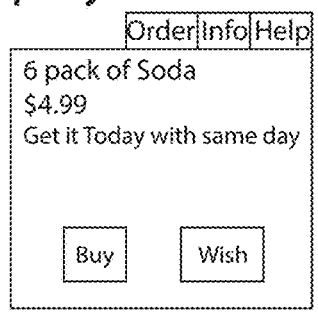
Figure 3C:
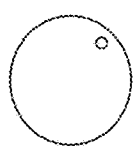
Figure 3C:
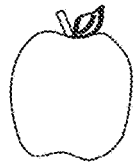
Figure 3C:
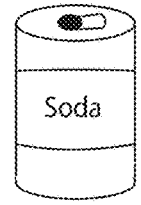
Figure 3C:
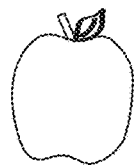
Figure 3C:
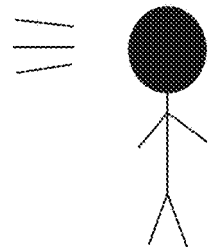
Figure 3C:
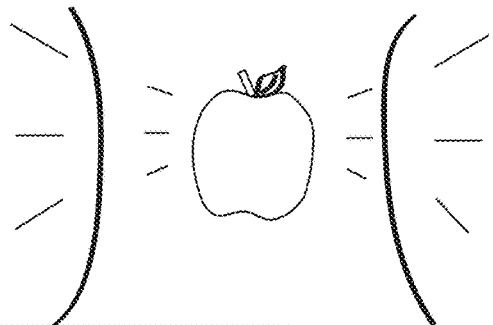
Figure 3C:
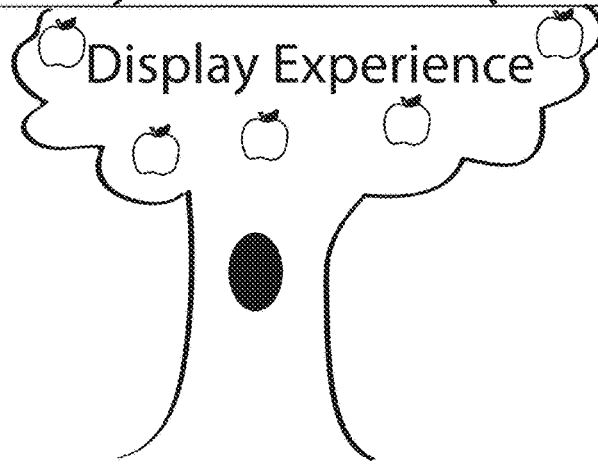

FIGS. 3A-3C depict various ad transitions according to embodiments of the present disclosure. While three types of results from transitions are depicted in FIGS. 3A-3C, as will be described further below, additional results may occur without departing from the present disclosure.

FIG. 3A depicts an ad transition to video according to an embodiment of the present disclosure. One or more objects may be spawned (step 301a), and in this embodiment, three objects (an orange, a soda can, and an apple) have been spawned. The user may gaze at the soda can to trigger a transition (step 302a), and once the soda can detects a raycast from collision, a transition may be started (step 303a). The transition may lead to display of an ad video (step 304a).

FIG. 3B depicts an ad transition to aCommerce according to an embodiment of the present disclosure. One or more objects may be spawned (step 301b), and in this embodiment, three objects (an orange, a soda can, and an apple) have been spawned. The user may gaze at the soda can to trigger a transition (step 302b), and once the soda can detects a raycast from collision, a transition may be started (step 303b). The transition may lead to display of an aCommerce (step 304b). As depicted in FIG. 3B, an aCommerce display include an offer (i.e., 6 pack of soda for $4.99), and the user can respond by selecting "Buy" or "Wish." If the user selects "Buy," the user may be prompted to confirm payment information. If the user selects "Wish," the offer may be added to a wish list maintained for the user to reference at a later time. The user also can seek more information about the offer/product being offered (i.e., "Info") and/or he/she may seek assistance (i.e., "Help").

FIG. 3C depicts an ad transition to an experience according to an embodiment of the present disclosure. One or more objects may be spawned (step 301c), and in this embodiment, three objects (an orange, a soda can, and an apple) have been spawned. The user may gaze at the apple to trigger a transition (step 302c), and once the apple detects a raycast from collision, a transition may be started (step 303c). The transition may lead to display of a display experience (step 304c). In this embodiment, the display experience may depict the room as an apple orchard with many trees throughout the environment.

As previously mentioned, systems and methods according to embodiments of the present disclosure may be utilized for various purposes/uses. As will be discussed below, embodiments of the present disclosure may be utilized with respect to advertising, wallet-type applications, incentives, commerce, tagging, as well as other non-categorized uses.

Advertising

Embodiments of the present disclosure may provide systems and methods that may be used with respect to advertising. Some embodiments of the present disclosure may provide for transformation of a holographic object into an advertisement. When referring to an "advertisement," it should be appreciated that it may include, but is not limited to, an experience, video, commerce, character, and combinations of the same. In some embodiments of the present disclosure, one or more logos may be displayed, and then, through computer vision technology, occlusion of the one or more logos may occur. Upon occlusion, the one or more logos may be replaced by one or more advertisements for products and/or competitors.

It should be appreciated that adjustments to an advertisement may be made based on one or more factors. These factors may include, but are not limited to, adjusting the optimal height of the advertisement display, adjusting speed at which an advertisement plays, adjusting the advertisement based on presence of more than one user, adjusting the speed and direction of an ad object, adjusting the size of the ad, and combinations of the same. Each of these adjustments will be described in further detail below. While each of these adjustments are described herein in the context of advertisements, it should be appreciated that adjustments may be made to other experiences without departing from the present disclosure.

An adjustment of the optimal height at which an advertisement is displayed may be made based on a user's height using an algorithm that calculates height by the orientation of the head of the user and a combination of the walls, floor, and ceiling. By being able to adjust the optimal height at which the advertisement is displayed, the user may be more likely to view the advertisement at eye level, thereby increasing the likelihood of the user being impacted by the advertisement.

It should be appreciated that users sometimes process advertisements at different speeds. This may be due to factors such as the age of the user, how fast the user can read, and/or whether the user is a visual or auditory learner. Thus, in some embodiments of the present disclosure, the speed at which an advertisement is played may be adjusted based on engagement traced by the user's gaze. When the user's gaze or movement is slower, then the advertisement might be slowed down to allow the user to experience it more fully.

In certain embodiments of the present disclosure, advertisements may be adjusted based on the presence of multiple users. If more than one user is present and available to view advertisements, it may be necessary to allow an advertisement to begin playing at a different time for each user. Additionally or alternatively, the same advertisement may be displayed to more than one user, but the advertisement may be set to repeat so that a user that begins viewing in the middle of the advertisement may be able to see the advertisement in its entirety after it has played through the first time.

In additional embodiments of the present disclosure, the speed and direction that an ad object moves may be adjusted. This adjustment may be based on the duration of time since the user has viewed an advertisement. Accordingly, if the user has been looking in a direction where an advertisement has not been displayed, systems and methods may be provided to direct an advertisement in the direction where the user is looking. Additionally or alternatively, the speed at which an ad object appears may be increased so that a user may view another advertisement faster than he/she may be presented with an advertisement based on his/her direction of view at the time. In other embodiments of the present disclosure, the size of an ad object may be adjusted based on the elapsed time without a gaze. Thus, if the elapsed time without a gaze has reached a predetermined amount of time (i.e., 2 minutes), then the size of the ad object may be increased to improve the chances that the user may direct his/her gaze toward the ad object. Some embodiments of the present disclosure may provide that additional advertisements may be spawned into the environment based on time elapsed without a gaze. In further embodiments of the present disclosure, the size of an advertisement may be adjusted based on the engagement level of the user.

It should be appreciated that the placement of an ad object may be optimized based on traced gaze patterns in embodiments of the present disclosure. In some embodiments of the present disclosure, the optimal number of ad objects to spawn within a given environment may be determined based on size using spatial mapping data. An ad object may be placed in an optimal location based on a predicted pattern of gaze.

With respect to advertising, there may be embodiments of the present disclosure where developers may make adjustments so that advertisements may be triggered in a certain way or in a specific location. For example, developers may be allowed to trigger the spawn of an advertisement through application interfaces based on experiences that have been created. In some embodiments of the present disclosure, developers may program an experience that triggers the user to turn in a different direction. Additionally or alternatively, developers may program an advertisement to spawn in a particular region of the environment that is attracting attention.

Embodiments of the present disclosure also may provide for modifications to be made to the advertisement itself. In an embodiment of the present disclosure, a character may be served to act as a representative for service, sales or advertisement for a particular company (advertiser). It should be appreciated that such a character may be a live representative streamed in real-time to the environment, may be a pre-programmed avatar with set talk tracks or it may utilize artificial intelligence to customize the talk tracks based on a user's tags, experiences and/or mood. It also should be appreciated that the physical appearance of an ad object may be customized based on one or more factors including, but not limited to, attractions of a user tagged by gaze pattern analysis, object analysis and/or human analysis.

It should be further appreciated that the types of information served in advertisements may be altered in embodiments of the present disclosure. In some embodiments of the present disclosure, real-time serving of product information, coupons and/or discounts may be provided depending on a calculated interest level of a user. Additionally or alternatively, advertisements may be served wherein a user may receive a reward that may be opened by a user and that may require the user to participate in an advertisement before the reward can be claimed. It should be appreciated that rewards may be given by character advertisements in some embodiments of the present disclosure. For example, a little monkey character may give a user a card that may open into a holographic screen playing an advertisement. If the advertisement is viewed by the user, the user may receive a reward. Users also may be provided with opportunities to hunt for one or more pieces or a specified computer vision-recognized object in an environment, such as a room or store. In another embodiment of the present disclosure, physical clothing may be occluded and replaced with advertisements and/or interactive experiences based on displayed branding. There also may be embodiments of the present disclosure that may provide for real-time two-way communication through a holographic user interface or a character within an advertisement. In such embodiments, feedback may be exchanged in one or more formats including, but not limited to, a visual format, an audible format and/or an interaction (such as through touch, gestures and/or motions).

There may be further embodiments of the present disclosure wherein advertisements may be situational. More specifically, situational advertisements may be served based on events triggered by computer vision. For example, if a user drops a glass and it shatters on the floor, an advertisement for a vacuum or broom to address the shattered glass may be displayed.

In additional embodiments of the present disclosure, an entity in control of a physical environment, such as a store or a building, may designated certain areas for revenue-shared virtual advertising. For example, an entity may own a building that has a large surface wall where virtual advertising may be displayed. The entity may contract with an advertiser to utilize that large surface wall for display of virtual advertising, and revenue generated from the virtual advertising on the large surface wall may be shared by the wall owner and the advertiser, among others.

Wallet-Type Applications

In addition to, or instead of advertising, systems and methods of the present disclosure may be used for wallet-type applications. In some embodiments of the present disclosure, crypto currency may be transferred via a motion or gesture toward a physical object, holographic object, location, company logo, website content, or other person. There may be embodiments of the present disclosure where visualization of the transfer of money may be customized. In these embodiments, money may include, but is not limited to, crypto currency or credit card), and the transfer of money may be toward another user and/or a business entity. The amount of stored crypto currency may be visualized by way of a virtual tattoo located on a user's body in an embodiment of the present disclosure. It also should be appreciated that personal information may be shared via a motion or gesture toward a physical or holographic object in embodiments of the present disclosure. In these embodiments of the present disclosure, specific information can be chosen and/or restricted based on the user's comfort level, and the transfer may be done utilizing peer-to-peer transfer, a local node through a wireless connect, a transfer through traditional TCP/IP, or another similar type of transfer. In further embodiments of the present disclosure, sub-wallets may be created using crypto currency for objects of interest analyzed from computer vision and/or shown in advertisements. In these embodiments, sub-wallets may accept funds until a goal amount is reached to allow for purchase and automatic ordering of a product.

Incentives

Incentives may be provided or administered using systems and methods according to embodiments of the present disclosure. In an embodiment of the present disclosure, an action or gesture may be rewarded based on confirmed recognition from input using an AR/VR/MR headset and analyzed by computer vision technologies. In another embodiment of the present disclosure, feedback on an action or gesture may be provided based on confirmed recognition from input data gathered using an AR/VR/MR headset or BCI. It should be appreciated that an action or gesture may be audible and/or visual and/or sensory and/or provided from application interfaces without departing from the present disclosure.

Other embodiments of the present disclosure may provide reward systems for entities or participants. In an embodiment of the present disclosure, a reward system may be provided for entities including, but not limited to, locations, businesses, and users. In such a reward system, rewards (which may be points-based and/or monetary in nature) may be allocated to entities for confirmed recognition from input data gathered through an AR/MR/VR headset or BCI. In another embodiment of the present disclosure, a governmental entity (i.e., local, state, or national) or another entity may create a reward bucket and automatically reward participants based on one or more specified/set objectives. The one or more specified/set objectives may be based on recorded actions, and rewards may be awarded based on confirmed recognition from input data gathered by an AR/MR/VR headset or BCI.

Commerce

Systems and methods according to embodiments of the present disclosure may also be used in the commerce environment. In an embodiment of the present disclosure, data including, but not limited to, distance traveled to shop, types of stores visited, transactions made via a platform or out of band, and engagement level based on surveys and/or ad campaign participation, may be used. In this embodiment, a user may be prompted to provide suggestions or recommendations. Then, using demographic information and/or a user profile, a buying pattern may be suggested for users fitting a similar demographic and/or profile. In an embodiment of the present disclosure, data may be collected about a first user, including but not limited to the following: gender, age range, martial status, zip code where he/she resides, types of stores where he/she shops, and how often he/she shops at a given store or stores. Using this data, systems and methods according to embodiments of the present disclosure may provide suggestions as to stores for a second user to visit based on similarities in one or more items of data collected about the first user. For example, if the second user resides in the same zip code and is the same gender and/or age range of the first user, the second user may be provided with store suggestions based on data collected from the first user.

In other embodiments of the present disclosure, systems and methods may be utilized to comprehend and assign an interest level based on analyzing gaze patterns of one or more users. In further embodiments of the present disclosure, gaze frequency may be tracked using raycast. Further, time of frequently viewed interlinked objects may be tracked using more than one time-based channels. For example, a user may be shopping at a store and looking at more than one item. Systems and methods according to embodiments of the present disclosure may analyze the user's real-time reactions to each item viewed. There also may be embodiments of the present disclosure where the optimal duration of gaze and the pattern of gaze that may classify an object may be determined and understood. It should be appreciated that location may be relevant to determining the optimal duration of gaze and/or the pattern of gaze. Additionally or alternatively, systems and methods according to embodiments of the present disclosure may filter, categorize and/or store commerce objects of interest with respect to objects that do not attract the interest of a user.

Tagging

It should be appreciated that systems and methods according to embodiments of the present disclosure may be utilized to determine tags based on gestures and/or actions of a user. These tags may be determined using computer vision and/or sound and/or spatial and/or AR/VR/MR. For example, systems and methods may be used to analyze the frequency and duration of time that a user has looked at one or more objects using an AR/VR/MR device. Gestures may then be analyzed to evaluate the user's interest level, and when combined with computer vision techniques, tags may be yielded (i.e., "staring" for 10 seconds at a "distance" of 6 inches, "walking" with a pace of 3 mph on a trail in XYZ park drinking orange-flavored sports drink). User interests also may be merged based on assigned tags and relational association. In some embodiments of the present disclosure, tags may be collected from answers and general conversation. Further, the direction that a user gazes may be tagged and tracked for pattern analysis. Data may be tagged to a location/business in parallel with user-tagged data. For example, a user drinks a white-chocolate mocha at a certain coffee shop. A tag may be assigned to the user and to that certain coffee shop. Real-time tagging also may be performed, and tags may expire related to a user's mood based on one or more factors, including but not limited to, vocal tone, pitch, gaze pattern, gaze direction, posture (micro changes in height), movements, gestures and actions. In some embodiments of the present disclosure, a user's mood may be determined based on permanent and/or real-time tags.

Key

According to the embodiments of the present disclosure a public key and private key may be generated from an SECP256K1 elliptical curve. SECP256K1 refers to the parameters of the ECDSA curve used in Bitcoin and other cryptocurrencies, and is defined in *Standards for Efficient Cryptography* (SEC) (Certicom Research, http://www.secg.org/sec2-v2.pdf). It should be appreciated that keys may be derived from other elliptical curves or encryption technologies in further embodiments. A practical key may be considered a block of encrypted or unencrypted information comprised of a compressed or uncompressed public key and compressed or uncompressed encrypted private key combined with other data and embedded or stored within a folder, image, 3D object, and/or file on an augmented, mixed, or virtual reality platform. In embodiments of the present disclosure, the block of information may contain an indicator showing a profile to be the default for the purpose of use and/or a name of the profile, but it should be appreciated that the block of information may be expanded to contain other information for use as a profile for identification and authentication on an augmented, mixed, or virtual reality platform. The practical key may facilitate the storage and use of one or more blocks of information within a single or multiple folder(s), image(s), 3D object(s), and/or other files. The practical key may accommodate the "swapping" of an active or default profile as a new identity for a single user or to identify additional users of one device. The practical key may be transferred or duplicated to other devices and used for authentication and identification purposes across multiple operating systems or augmented, mixed, or virtual reality platforms. In the present disclosure, the private key may be encrypted by a password stored securely within one or more servers, but it should be appreciated that further embodiments may include local methods of encryption for the contained private key and the entire practical key. It should also be appreciated that while the practical key data may be appended to the data of an image containing a logo generated by a DLL, there may be other embodiments of the present disclosure that may include the obfuscation, encryption, and storage of the key within an image with or without a logo, standalone file, or appended to the data of another existing file. The public key component may be shared with others (people, businesses, and/or other entities) through an image, text, animation, or 3D object and stored on a list for quick identification, communication, and permissioned and/or non-permissioned sharing of content such as advertisements, experiences, scripted and non-scripted 3D objects, animated or still 2D images, appless apps or tools through an augmented, virtual, or mixed reality platform. In embodiments of the present disclosure, the practical key may be used for authentication on the PracticalVR platform, but it should be appreciated that other authentication systems may integrate use of the key by partnership with PracticalVR to authenticate users within applications, websites, or other mediums that require identification and verification of a user. The practical key may provide authentication for certain physical and digital services, experiences, scripted and non-scripted 3D objects, animated or still 2D images, appless apps, or tools from environmental mapping, range, geolocation, and proximity to location-locked objects as referenced herein. The practical key may also facilitate the transfer of identifiable or non-identifiable information containing text, images, 3D objects, and/or other representations of data without authentication. The transfers may happen over a public broadcast through a limited or wide range wireless connection, and/or physical conduction technology. In further embodiments of the present disclosure, there may be a permission system that may allow a user to customize what the practical key shares publicly. The user may customize permissions based on the practical key of other users or entities stored on the list referenced herein or being broadcast in an area over limited or wide range wireless connection, and/or physical conduction technology. In some embodiments, the permissions may have many levels of sharing attached such as a public view with limited information, a view for co-workers with additional information, a view for friends with even more information, and/or a view for family with more private information. It should be appreciated that permission views may be unlimited and/or could be customized to an individual or entity level. In some embodiments of the present disclosure, a user may choose to enter a mode that completely disables public and/or private broadcasts of information, disallowing all sharing through the key. The permissions may be customized through a 2D interface, 3D object, appless app, traditional application, website interface, tool, and/or commands invoked through gesture, keyword, gaze, eye movements, and/or other forms of input. The permissions may be stored on one or more server within a database and/or local on the device. A public broadcast may require a handshake procedure including the signing of a message utilizing the public and private key components and communication to one or more location-based nodes, and/or servers to verify the identity of the user and prevent spoofing of public keys. Physical and digital services, experiences, scripted and non-scripted 3D objects, animated or still 2D images, appless apps, and tools shared through the practical key may be stored on the local device, a location-based node within range, and/or on one or more servers. When another person or entity-based practical key comes within range, if allowed through the permission system referenced herein, objects may be streamed and/or downloaded from a node within range, one or more servers, or retrieved from a local cache of information stored on the device and/or a tethered storage device. Permission-based sharing utilizing the practical key may also work over the Internet for dynamic sharing or static not associated with a location-based event. For Internet-based sharing, a message may still be signed to verify identity and ownership of the public key to prevent spoofing. In some embodiments, the practical key may be used for communication via text, animations, object spawning, video, voice, or other forms of communication. When used for communication, the public key component of the practical key may act as identification for routing through one or more servers. Once authentication has been established, the server may then route a message to another user's practical key by also using the public key component to establish identity and route the message to the appropriate end user or entity.

The practical key may also include a blocking list, similar to the friends list previously discussed. When a user or entity is blocked, all forms of communications are ignored regardless of public permission settings, and in further embodiments the blocked end user, logo, or entity may be obfuscated from the environment using computer vision. The obfuscation may be in the form of an image, 3D model, filter, or other overlay on the blocked individual.

The practical key may be used to associate users with data, and it should be appreciated that the data may be anonymized and/or encrypted to prevent firm identification of the end user. The practical key may allow the end user or entity to review statistics from collected data such as software and/or physical actions or other collected data as referenced herein. Once authenticated using the practical key, statistics may be streamed or downloaded from one or more servers and/or stored locally on the device. The statistics may then be visually represented through a 2D interface, 3D object, appless app, traditional application, website interface, tool, synthesized voice, invoked through gesture, keyword, gaze, eye movements, and/or other forms of input. The practical key may also associate actions to a user's identity and add to goals, milestones, or other counters and allow rewards for achievement. In embodiments of the present disclosure, rewards may be in the form of microtransactions or visual feedback, but it should be appreciated that rewards may be defined as anything by a PracticalVR user, or an entity using the practical key. The practical key may transform one or more components into a functional crypto-currency wallet to facilitate microtransactions or other transactions as referenced within. It should be appreciated that the practical key may be fully compatible with all cryptocurrencies to date, and in future embodiments may change or add components to remain compatible.

Other

While many applications of systems and methods according to embodiments of the present disclosure have been categorized and described herein, it should be appreciated that there are other applications that may be provided. A user's gaze pattern may be recorded by analyzing the direction of the user's gaze and any changes in direction of the gaze. Physical items or attributes such as clothing, hair color and/or hair style may be occluded and/or replaced in embodiments of the present disclosure. In some embodiments of the present disclosure, a user's first person camera view may be combined with a detailed room snapshot and spatial mapping data to allow a remote user to have an accurate telepresence experience. In other embodiments of the present disclosure, a user may visualize and customize a holographic representation of the creation, transfer, and/or deletion of data. For example, a text document may be transformed into a paper airplane and thrown across the room or a virtual document may be deleted by throwing it towards a physical trashcan. Embodiments of the present disclosure also may allow interactive experiences as a shell of documents. For example, a developer may create a visualized experience of how his/her document is opened. Password restrictions on documents may be visualized in embodiments of the present disclosure.

In some embodiments of the present disclosure, ultrasound may be emitted from a headset. That ultrasound may be used to render a real-time representation of the human body for interaction with virtual objects, placement of virtual objects, and/or transmission of presence to virtual applications.

Other embodiments of the present disclosure may provide systems and methods to search databases of information on the fly using real-time data fed from an AR/VR/MR headset. This real-time data may be combined with stored interests for more accurate results. This may be utilized for near-instant responses to questions asked, requests for additional information, and/or community impressions. For example, a politician may use real-time information fed through an AR/VR/MR headset or BCI to gain a better understanding of a proposed question, view statistics, and/or craft a more informed answer.

Systems and methods according to embodiments of the present disclosure may provide a centralized node such that, upon receipt of permission from a user, the centralized node may provide additional wireless computing power for enhanced rendering. Use of a centralized node may allow one or more users to share experiences.

Further embodiments of the present disclosure may provide for real-time translation and occlusion of natural language in a textual format. In these embodiments, the text may be partially changed into a foreign language that the user is attempting to learn. The text may also be completely translated for native language reading. There may be varying levels of occlusion to provide a mixed language learning experience for the user.

Additional embodiments of the present disclosure may provide for creation of channels that may allow entities (i.e., a person, a building, and/or a location) to share content and placement of content with users that subscribe to the channels. The sharing could be controlled by one or more local nodes, one or more cloud-connected servers, or hosting may be done ad-hoc on the device itself. It should be appreciated that a virtual machine may be created to run on at least one local node or in the cloud leaving the AR/VR/MR/BCI device to act as a remote interface for the experience in some cases. In other cases, the device may handle and compute data sent from the cloud or local node to show the experience. It should be appreciated that a local node may be a device that sits within a location and pushes content wirelessly to the user with permission. In some embodiments, a local node may handle computations and renderings and then stream the data to the device in real time. Upon entering an area with at least one local node and detecting it via wireless communication technologies, the user may be presented with a choice to connect to the at least one local node and join the local channel. Locations that host local nodes could charge a small fee for use. At least one local node may also be connected to one or more cloud-based servers to ensure that all channel subscriptions are known. It should be appreciated that there may be private channels that may allow entities to share experiences privately within public places. For example, a user may walk into a coffee shop that has at least one local node and channel set up. The user is prompted to connect to the at least one local node and authorize the channel's experience. Once connected, the user can experience the coffee shop that may be pre-themed with games, art and different backgrounds. If the user elects to tune to the pre-themed channel, the user would see the coffee shop as the administrator has established the channel.

Embodiments of the present disclosure may provide for extension applications from a tethered or connected computer to augment features of a main application by providing additional displays, tools and/or objects for interaction. For example, a mini-map for a game may be holographic as opposed to taking up monitor real estate.

In another embodiment of the present disclosure, a user may customize sharable widgets on a profile. The user may provide open public access or he/she may manage restrictions choose other users with which to share. The user may choose the location of the widget on his/her body in a general area. For example, a user may place a widget on his/her chest that may display heart rate. A user also may customize holographic tattoos or an avatar but may restrict with whom the tattoos or avatar may be shared.

Further embodiments of the present disclosure may allow a user to generate and throw a screen with chosen content to a point within a physical location that places the screen on a local channel for sharing with other users. This local channel may specify permissions on who can perform certain tasks, such as moving, editing, adding and resizing content.

In another embodiment of the present disclosure, a user may customize a connection with language and different effects that may visible to others. When spoken by the user, the triggered word may display the effect or emoji to other users on the same channel. For example, when a user says the word "angel," a halo may appear above his/her head.

Embodiments of the present disclosure may collect data but also deploy 3D objects to users. Accordingly, shared holographic experiences may be enabled across all platforms and devices, thereby making social sharing seamless within mixed reality. If a user walks into another user's house, he/she should be able to instantly see the same "themed room" and/or game being played. Thus, a user should not have to download and run an app exclusively to see simplistic or ambient things in mixed reality in embodiments of the present disclosure. Further, the practical key may enable lightweight appless apps, such as a wallet, navigation or restaurant menu, to be deployed to a user inside of another experience. Through APIs according to embodiments of the present disclosure, developers may create appless apps and other shared experiences. Users may create preferences and see these tools or ambient experiences deployed inside of a primary application according to embodiments of the present disclosure.

Other embodiments of the present disclosure may use the practical key to allow an employer to pay an employee in real-time as he/she completes work or a city to incentivize citizens to pick up trash around the city. Accordingly, users may depend on the practical key to share experiences and use any appless apps that they need. When users use the practical key, data may be collected to enable an artificial intelligence engine to recognize, confirm, and reward almost any action—software and physical.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for spawning or transformation of an object or an interface on action by a user on an augmented, mixed or virtual reality platform upon authentication of the user, the method comprising:
    starting a practical event manager, wherein a session is created and the user is identified;
    placing one or more anchors to a precise location for real-time deployment in a main experience and for the one or more additional experiences;
    loading location-locked objects or placing an object dynamically into an environment being viewed by the user in the main experience, wherein the object passively waits for a collision with a raycast from the user or interaction via action by the user; and
    starting a transition once the object detects the raycast from collision or action, wherein the transition transforms the object into the one or more additional experiences.

2. The method of claim 1 further comprising:
    placing a duplicate object into the environment after a period of time has passed and no collision with the raycast or action has occurred.

3. The method of claim 1, wherein when the transition starts, the main experience enters a frozen state to prevent interruption of the main experience.

4. The method of claim 1, wherein the one or more additional experiences are selected from the group comprising:
    a video, a character, a billboard, aCommerce, a survey, a 3D model, 2D interface, an animated or non-animated image, an experience, or other interface for input.

5. The method of claim 1, wherein upon authentication of the user, data is collected from the user, the data including tags based on gestures and/or actions of the user, gaze patterns of the user, duration of gaze of the user, distance traveled to shop, types of stores visited, transactions made via the augmented, mixed or virtual reality platform, engagement level based on surveys, placed or spawned location of experiences, scripted or un-scripted 3D objects, animated or still 2D image, appless app, and/or tool, and/or ad campaign participation.

6. The method of claim 1, wherein the user is identified through the following steps:
  upon connection between a client and at least one server after the user launches an application on the augmented, mixed or virtual reality platform, checking to see if an existing practical key for the user is stored;
  using the existing practical key, reading a public key and an encrypted private key;
  sending the public key to the at least one server;
  receiving a saved password;
  decrypting the private key and signing a message to include a cryptographic signature;
  sending the cryptographic signature to the at least one server for verification;
  receiving a new password from the at least one server, wherein the new password is used to re-encrypt the private key;
  notifying the at least one server that an encrypted practical key has been saved; and
  receiving confirmation that the user is authenticated.

7. The method of claim 1, wherein the action is selected from the group comprising:
  gaze, keyword, hand gesture, computer vision recognized object, eye movements, or other user-controlled action.

* * * * *